United States Patent
Yang et al.

(10) Patent No.: US 7,723,571 B2
(45) Date of Patent: May 25, 2010

(54) METHOD OF EXPRESSING SMALL PEPTIDES USING CEREAL NON-STORAGE PROTEINS AS FUSION CARRIER IN ENDOSPERM AND THE USE THEREOF

(75) Inventors: Daichang Yang, Wuhan (CN); Tingting Xie, Wuhan (CN)

(73) Assignee: Healthgen Biotechnology Inc. in Wuhan, Hubei Province (CN)

( * ) Notice: Subject to any disclaimer, the term of this patent is extended or adjusted under 35 U.S.C. 154(b) by 0 days.

(21) Appl. No.: 11/810,863

(22) Filed: Jun. 6, 2007

(65) Prior Publication Data

US 2007/0289033 A1 Dec. 13, 2007

(30) Foreign Application Priority Data

Jun. 8, 2006 (CN) .................. 2006 1 0019285

(51) Int. Cl.
*C12N 15/82* (2006.01)
(52) U.S. Cl. .................. 800/288; 800/287; 536/23.4
(58) Field of Classification Search ................ None
See application file for complete search history.

(56) References Cited

U.S. PATENT DOCUMENTS

2008/0010697 A1* 1/2008 Yang et al. .................. 800/260

FOREIGN PATENT DOCUMENTS

WO WO 99/16890 * 4/1999

OTHER PUBLICATIONS

Samuelsson et al. Chaperone-like effect during in vitro refolding of insulin-like growth factor I using a solubilizing fusion partner. (1996) Annals of the NY Acad. Of Sci. ; vol. 782, pp. 486-494.*

Ciaffi et al. Cloning and characterization of wheat PDI (protein disulfide isomerase) homoeologous genes and promoter sequences. (2006) Gene; vol. 366, pp. 209-218.*
Liu et al. Increase of soluble expression in *Escherichia coli* cytoplasm by a protein disulfide isomerase gene fusion system. (2005) Protein Expression and Purification; vol. 44, pp. 155-161.*
De Bree, F. et al. (1998) "Preparation and characterization of the recombinant selenomethionine analogue of insulin-like growth factor-I" *Protein Expression and Purification* 13:319-325.
Dobeli, H. et al. (1998) "Recombinant fusion proteins for the industrial production of disulfide bridge containing peptides: purification, oxidation without concatamer formation, and selective cleavage" *Protein Expression and Purification* 12:404-414.
Einhauer, A. et al. (2001) "The FLAG™ peptide, a versatile fusion tag for the purification of recombinant proteins" *J. Biochem. Biophys. Methods* 49:455-465.
Papaioannou, M. et al. (2002) "Protein-protein cross-linking in the use of the eukaryotic eGST-fusion system" *Protein Expression and Purification* 26:462-466.
Savage, M. et al. (2005) "IGFs and IGFBPs in GH insensitivity" *Clinical Management* 9:100-106.

* cited by examiner

*Primary Examiner*—Cathy Kingdon Worley
(74) *Attorney, Agent, or Firm*—Knobbe Martens Olson & Bear LLP

(57) ABSTRACT

The present invention provides a method of using cereal non-storage protein as fusion carrier to highly express small peptides in host endosperm cells. The method includes the steps of providing an endosperm-specific promoter and a DNA leading sequence encoding an endosperm-specific signal peptide; providing the gene of a non-storage protein as fusion carrier and an target gene; constructing a expression vector containing the promoter and DNA leading sequence, the gene of the fusion carrier, and a target gene; and expressing the expression vector in a host endosperm cell. Also provided in the invention are a vector constructed there from and the use thereof.

9 Claims, 8 Drawing Sheets

T1 transgenic seed

US 7,723,571 B2

METHOD OF EXPRESSING SMALL PEPTIDES USING CEREAL NON-STORAGE PROTEINS AS FUSION CARRIER IN ENDOSPERM AND THE USE THEREOF

CROSS-REFERENCE TO RELATED APPLICATIONS

This application claims the benefit of Chinese Patent Application No. 200610019285.9, filed Jun. 8, 2006.

FIELD OF THE INVENTION

The present invention relates to the field of gene engineering. Particularly, the present invention relates to a method of expressing small peptides in endosperm using cereal non-storage proteins as fusion carriers and the use thereof, i.e., a method in which endosperm cells of cereals such as rice and barley were used as bioreactors and protein fusion strategy was applied to introduce the endosperm-specific expression cassette using any non-storage proteins (e.g., Bip and PDI from cereal crops) as the fusion partners into rice or barley cells, which leads to massive accumulation of the small peptides in endosperm cells of a transgenic rice or barley. The present invention also relates to plant source peptides produced by the method.

BACKGROUND OF THE INVENTION

Small peptides refer to those with less than 100 amino acids in length. In recent years, small peptides were widely used in the fields of medicine, disease treatment, molecule vaccine, etc., which include surface antigens, disease diagnosis, and treatment of AIDS and cancers. With the fast development of biotechnology, more and more small peptides were discovered. Accordingly, a large amount of peptides are needed to meet the requirement in a variety of industries such as functional research, clinical experiment, and disease treatment. Generally, chemical synthesis is the main route to produce peptides with less than 40 amino acids in length. During the process of chemical synthesis, due to the existence of certain incomplete chemical reactions and chemical modifications, even peptides with less than 40 amino acids are difficult to be synthesized (Dobeli, et al., 1998 *Protein Expression & Purification*, Vol. 12:404-414). Therefore, it became advantageous and necessary to utilize bio-system to produce peptides.

In 1950s, bacteria were used as bioreactors to produce pharmaceutical products. However, because bacteria are prokaryotes, which do not possess the processing system of eukaryote, its application are seriously limited for some proteins whose bioactivities rely on protein modification. As the second-generation bioreactor, yeast has come into use in the production of medicine product since 1970s. However, the problems of low yield and incomplete modification/processing seriously limited the extensive use of yeast. The third-generation bioreactor utilized higher plant and animal cells. Presently, eukaryote bioreactors are categorized into animal bioreactors and plant bioreactors, and animal bioreactor further includes cell culture and transgenic animal. Currently, major antibodies for pharmaceutical use are produced by CHO (or mice) cell line culture. The studies of transgenic animals mainly focus on the expression of recombinant protein in breast cells of transgenic cow or egg albumin. However, the problems of animal pathogens contamination, high cost, and high investment requirement severely limit their use. It is estimated that the maximum productive capacity of monoclonal antibody is about 1,000 kg per year worldwide. To obtain another 1,000 kg, 40 billion US dollars of investment and more that ten years of time are further needed. All these data indicate the current productive system and productive capacity of the recombinant protein is far from enough to meet market requirement. Accordingly, a highly efficient and safe expression system is needed to satisfy the huge market demand of small peptide production.

In most cases, peptides with at least 80 amino acids are needed for recombinant protein expression. Even in such a case, the expression level is rather low. Therefore, a major way to improve the expression level of the peptide is to use fusion protein strategy. Up to now, the studies on fusion protein expression systems are mainly suitable for *Escherichia coli* (*E. coli*) and yeast systems. For instance, maltose binding protein (MBP), FLAG (Einhauer et al. 2001 *J. Biochem. Biophys. Methods*, Vol. 49:455-465) and glutathione (GST) (Papaioannou et al. 2002 *Protein Expression & Purification*, Vol. 13:462-466) were used as fusion partners in *E. coli* and yeast. Although some fusion protein expression systems have been commercialized, they were merely used in basic researches in, labs. Studies on the expression of peptides in plant expression system are relatively new and have not achieved much progress so far. Recently, it has been reported that the fusion carrier of disulfide bond dismutase (PDI) and green fluorescence protein (GFP) was used to express peptide. Unfortunately, the expression level was quite low. On the other hand, many peptides have been successfully expressed in *Escherichia coli* and yeast systems, there existed an obvious risk of being contaminated by pathogens from hosts. Moreover, the problems of low expression level and formation of insoluble inclusion bodies in *E.coli* cells, and higher molecular weight of the fusion partners used in prokaryotes cause troubles to downstream processing and therefore are not suitable to be used in eukaryotes, especially higher plant cells. Though plant cells have been used to express peptide, the low expression level has always been a bottleneck problem in the researches.

Due to the defects and limitations mentioned above, to develop fusion protein expression vectors in higher plants becomes increasingly important. Using higher plant as bioreactor has the advantages of low cost, high level expression, easy to scale up, free of pathogen contamination, etc, making it a promising candidate for future peptide production. So far, due to the problems of relatively high molecular weight, lack of cell organelle transportation signals, etc., prokaryotes fusion expression systems are not suitable for expressions in higher plant cells. Therefore, it is of significance to explore and develop small peptide expression system that is suitable for higher plants. Using rice storage protein as fusion carrier, Ventria Bioscience Inc. in USA has successfully expressed small peptides. Nevertheless, though higher level expression was achieved by the company with the use of globulin as fusion protein carrier, its application was limited in many aspects since the use of globulin to express peptide caused solubility problems. Other than storage proteins, another two proteins massively expressed in rice endosperm are endoplasmic reticulum biding protein (BiP) and protein disulfide bond dismutase (PDI), both of which are stored in protein body I. The C-terminus end of Bip protein has molecular chaperone activity, facilitating the correct folding of protein into functional protein conformation. Using C-terminus of Bip protein as fusion carrier can not only accumulate the fusion protein inside protein bodies (similar to the accumulation of the storage protein in protein bodies), but also increase the solubility of the fusion protein, thus overcoming the problem of insolubility resulting from using storage protein as fusion carrier in conventional methods. Another non-storage protein that highly expresses in rice or wheat endosperm is protein disulfide isomerase (PDI). PDI has two functions. One is disulfide dismutase activity at N terminus, and the other is C-terminal possesses molecule chaperone activity. Accordingly, using its C terminal as fusion protein carrier can also achieve the purposes of improving both the expression and the solubility of the protein. By using C-terminal of non-storage protein PDI and Bip as fusion carrier which are expressed specifically in endosperm, the present invention can not only improve protein expression level but also overcome the solubility problem existed in other international patents where storage proteins were used as fusion proteins, thus conferring innovativeness and patentability to the present invention.

Insulin-like growth factor (IGFs) is one of the most important growth factors involved in various types of proliferations and metabolisms. It not only takes an important role in the growth of human skeleton, but also facilitates the maturation of relevant cells and associates with wound healing. IGF-1 is a single strand peptide with 70 amino acids, with 3 disulfide bonds and no glycosylation site (De Bree, et al. 1998 *Protein Expression & Purification*, Vol. 13:319-325). Based on the analysis of the position of the recognizable disulfide bond, it is believed that the secondary structure of IGF-1 could be similar to that of insulin, both of which have same conservative glycines in same positions and have similar nonpolar amino acid residue core. IGF-1 is widely used in clinics. Recombinant human IGF-1 (rhIGF-1) and its complex have been effectively used in treating growth hormone insensitivity syndrome (GHIS), which includes GH receptor deficiency, IGF gene deficiency, and block of signal transduction path of growth hormone. Moreover, IGF-1 has been used to treat patients suffered from type I or type II diabetes or patients with severe insulin resistant symptoms. With the administration of rhIGF-1, the symptoms were greatly relieved. rhIGF-1 or its complex rhIGF-I/IGFBP-3 can be further used to treat chronic inflammation, nutrition disorder, and other conditions such as Crohn's disease (also called segmental enteritis), juvenile chronic arthritis, bladder/gall bladder fibrosis, etc. Relevant studies on the pharmacodynamics of IGFs are very limited, however, the shortage of IGFs supply is believed to be one of major problems (Savage, et al. 2005 *Edocr. Development.* Vol. 9:100-106).

SUMMARY OF THE INVENTION

Therefore, it is an object of the present invention to solve the defects of low level expression, poor solubility, poor bioactivities, unsafety, etc. existed in conventional bioreactors where prokaryotic and eukaryotic organism were used as hosts. According to the present invention, since the C-terminal of Bip or PDI (non-storage proteins of cereals) has molecule chaperone function, they were used as fusion carriers to fuse with small target peptides. Under the control of rice endosperm-specific promoter and signal peptide, the expressed fusion protein entered into the endomembrane system of rice endosperm cells and stored in the protein body of the rice endosperm. As a result, a large amount of fusion proteins accumulated to a high level in rice seed. The present invention can not only solve the problems of low level expression, poor solubility, poor bioactivities, unsafety, etc existed in conventional expression systems, but also avoid the problem of pathogens contamination from animal cells.

One object of the present invention is to provide a method, in which the promoter and signal peptide of rice glutelin gene Gtl3a are used to make the fusion protein expression cassette specifically expressed and store in protein body of rice endosperm cell. The method can prevent the fusion protein from being attacked by proteases in cytoplasm and allow the accumulation of the protein in rice endosperm, thereby producing the protein in high yield.

By utilizing the molecule chaperone functional domain of the C-terminal of Bip and PDI of cereal non-storage protein as fusion carrier, another object of the invention is to improve both the expression level and solubility of fusion protein in endosperm cells. A further object of the invention is to set up a new technique platform for efficiently expression small peptides in endosperm cells of cereals such as rice or barley. With this platform, it is easy to obtain such an expression system, which is safer, pathogen-free and easy to scale up compared to those of transgenic cow and chicken. Furthermore, it is also cost-effective and can produce fusion protein in higher yield.

It is another object of the present invention to provide the use of cereal non-storage protein as fusion carrier to express IGF-1 in rice and barley endosperms. The fusion carrier and target genes were optimized to rice preference genetic codons, so that the expression level could be improved in rice endosperm cells.

BRIEF DESCRIPTION OF THE DRAWINGS

FIGS. 5 and 6 illustrate the results of polyacrylamide gel staining and Western blot of the recombinant fusion protein expressed in rice endosperm. The recombinant fusion protein was extracted from the transgenic rice endosperm. Eleven T1 generation were obtained from transgenic strain #26-13, and 1 ml of protein extracting buffer was used to extract the total protein from single seed. Ten μl sample was loaded onto 12% polyacrylamide gel. After electrophoresis, Coomassie Blue staining and Western blot were used to show the results.

FIGS. 8 and 9 illustrate the results of polyacrylamide gel staining and Western blot of the recombinant fusion protein expressed in rice endosperm. The recombinant fusion protein was extracted from the transgenic rice endosperm. Thirteen T1 seeds were obtained from transgenic strain #25-12, and 1 ml of protein extracting buffer was used to extract the total protein from single seed. Ten μl sample was loaded onto 12% polyacrylamide gel. After electrophoresis, Coomassie Blue staining and Western blot were used to show the results.

BRIEF DESCRIPTION OF THE SEQUENCES

SEQ ID NO: 1 is the promoter sequence of rice glutelin gene Gtl3a.

SEQ ID NO: 2 is the vector specifically expressed in rice endosperm.

SEQ ID NO: 3 is the nucleotide sequence of the C-terminal of chemically synthesized rice preference codons of Bip.

SEQ ID NO: 4 is the nucleotide sequence of the C-terminal of chemically synthesized rice preference codons of PDI.

SEQ ID NO: 5 is the nucleotide sequence of the C-terminal of chemical synthesized rice preference codons of IGF-1.

SEQ ID NO: 6 is the forward primer of rice CP promoter used in PCR.

SEQ ID NO: 7 is the reverse primer of rice CP promoter used in PCR.

SEQ ID NO: 8 is the forward primer of hygromycin phosphotransferase gene used in PCR.

SEQ ID NO: 9 is the reverse primer of hygromycin phosphotransferase gene used in PCR.

DETAILED DESCRIPTION OF THE PREFERRED EMBODIMENT

The invention will be further illustrated in detail in the following descriptions.

A. Obtaining of Endosperm-Specific Promoter and Signal Peptide from Rice Genome

Through biological information analysis, a strong promoter of Gtl3a gene, a member of rice glutelin gene family, was found. In order to obtain Gtl3a promoter and its signal peptide sequence, a pair of primers (SEQ ID NO: 1 and SEQ ID NO: 2 of China Patent Application number 200510019084.4), which is hereby incorporated herein by reference were synthesized according to the information provided from Genbank Gtl3a (accession number: AP003256) for PCR amplification. For the convenience of cloning, a restriction site for cohesive end was added to the 5' end of the forward primer, and another restriction site for blunt end was added to the 3' end of the reverse primer. Genomic DNA extracted from the leaves of rice variety Taipei 309 was used as template for PCR. Using the primers, a DNA fragment with 1284 base pairs in length was obtained following standard PCR protocol. DNA sequencing analysis indicates the fragment is identical to the sequence of Genebank and has a typical promoter structure. Thus, the Gtl3a promoter and signal peptide sequence that can be used to control the expression of recombinant protein in cereal endosperm cell was produced (SEQ ID NO: 1).

B. Construction of Rice Endosperm-Specific Expression Cassette

Figure 1:
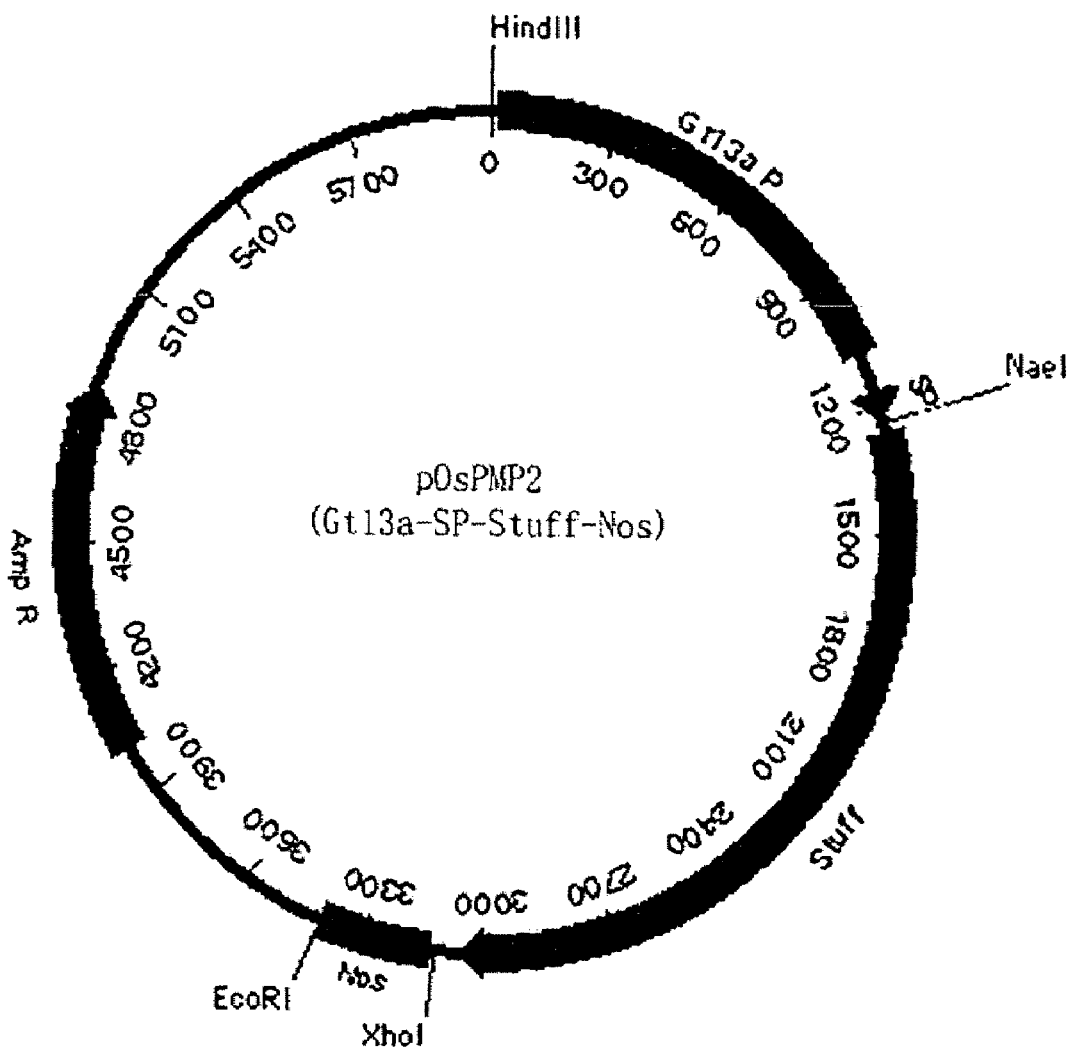
FIG. 1 is the restriction map of rice endosperm-specific gene expression vector pOsPMP2 (Gtl3a Sp-Stuff-Nos).

After obtaining the Gtl3a promoter and signal peptide sequence as described above, the PCR product was digested with cohesive end and blunt end restriction endonucleases, followed by ligation reaction with pBI221 (Clontech) digested by the same restriction endonucleases. The ligation mix was electroporated into *Escherichia coli* strain DH10B (Invitrogen). The resulting plasmid designated as pOsPMP2 (See FIG. 1) contains Gtl3a promoter, Gtl3a signal peptide, and Nos terminator, with the nucleotide sequence shown in SEQ ID NO.2.

C. Optimizing Genetic Codon of the Fusion Carrier and Target Gene and Synthesizing Thereof The C-terminal nucleotide sequences of rice Bip gene (Genebank accession number: AAB63469), wheat PDI gene (Genebank accession number: AJ277377) and insulin-like growth factor 1 gene (Genebank accession number: CAA01955) were obtained from the Genebank of National Center of Biotechnology Information (NCBI). Analytic software MacVecter (product of Accelrys) was used to covert the genes into rice preference genetic codons. The optimized genes were then synthesized by Blue Heron Biotechnology incorporation in USA. The C-terminal of-thus obtained rice preference rice Bip gene has the sequence shown in SEQ ID NO: 3. The C-terminal of thus obtained rice preference wheat PDI gene has the sequence shown in SEQ ID NO: 4. The sequences of thus obtained rice preference human IGF-1 gene has the sequence shown in SEQ ID NO: 5. Compared to their original nucleotide sequences, the ratio of changed sequences of the optimized genes ranges from 11.2 to 21.4%, and that of the genetic codons ranges from 30.5-54.3%. In contrast, the amino acid sequences remain unchanged (see Table 1).

TABLE 1

Comparison among optimized fusion carriers and target gene

| Items | Bip-C | PDI-C | IGF-1 |
|---|---|---|---|
| Nos of genetic codes in total | 256 | 133 | 70 |
| Nos of genetic codes changed | 78 | 64 | 38 |
| Ratio of genetic codes changed (%) | 30.5 | 48.1 | 54.3 |
| Nos of deoxynucleotides in total | 768 | 399 | 210 |
| Nos of deoxynucleotides changed | 86 | 67 | 45 |
| Ratio of deoxynucleotides changed (%) | 11.2 | 16.8 | 21.4 |
| Ratio of amino acids changed (%) | 0 | 0 | 0 |

For the convenience of gene cloning, a blunt end and a cohesive end restriction sites were added to 5' and 3' ends respectively during gene synthesis.

D. Construction of Various Vectors for the Expression of Fusion Proteins

1). Construction of pOsPMP25(Gtl3a-PDIC-IGF-1-Nos): pOsPMP2 DNA was firstly digested by MscI and XhoI. Then, optimized gene of human IGF-1 amplified via PCR amplification was cloned into pOsPMP2. The resultant was used to transform *E.coli* strain DH10B to produce resultant pOsPMP3, an intermediate plasmid containing IGF-1 gene. pOsPMP3 DNA was further digested by NaeI and NcoI, after which the DNA fragment of PDIC amplified by PCR was cloned into pOsPMP3, the resultant plasmid is designated as pOsPMP25 (Gtl3a-BipC-IGF-1-Nos).

2). Construction of pOsPMP26 (Gtl3a-BipC-IGF-1-Nos): pOsPMP3 DNA was firstly digested by NaeI and NcoI. Then, BipC DNA was cloned into pOsPMP3 after PCR amplification to produce resultant plasmid pOsPMP26 (Gtl3a-BipC-IGF-1-Nos).

3). Construction of vector With selectable marker genes: The promoter of Cysteine proteinase β 3 (CP) was used to mediate the callus-specific expression of a selectable marker gene, encoding hygromycin phosphotransferase during tissue culture after transformation. A pair of primers was synthesized (SEQ ID NO.6 and SEQ ID NO.7), with HindIII and SmaI restriction sites added to the ends of each primer. The genome of rice variety Taipei 309 was used as DNA template based on a standard PCR protocol, and a 1,103 bp fragment containing promoter was obtained by PCR amplification. The fragment was digested with HindIII and SmaI, and then ligated with pBI221 (Clontech) which was digested by the same restriction enzymes. The resultant containing CP promoter sequence was used to transform $E.$ $coli$ strain DH10B to produce intermediate plasmid designated as pOsPMP4. Hygromycin β Phosphotransferase (Hpt) was used as a selectable marker, which is obtained from pCAMBIA1301 (CAMBIA company from Australia). To obtain the gene fragment of Hpt, pCAMBIA1301 was used as a template following the standard PCR protocol, with a forward primer (SEQ ID NO: 8) and a reverse primer (SEQ ID NO: 9), wherein restriction site SmaI was added to the forward primer and restriction site XhoI was added to the reverse primer. The resultant gene fragment of Hpt was digested with SmaI and XhoI, while pOsPMP4 DNA was digested with NaeI and XhoI. Then, the gene fragment of Hpt was ligated with the DNA fragment of pOsPMP4 (containing CP promoter) digested by NaeI and XhoI. Finally, the resultant was used to transform $E.$ $coli$ strain DH10B to produce pOsPMP5, an expression vector guiding a selectable marker specifically expressed in rice callus.

Genetic Transformation of Rice Gene:

The husks of rice seed were removed and the seed was sterilized in 20% sodium hypochlorite for 20 minutes, followed by rinsing three times with sterilized water. The seed was then cultured on callus induction culture medium for 20-25 days to produce calli. The induced calli were then transferred to a PR medium to culture for another 9-10 days before used for future transformation. For DNA coating, 0.5 μg of pOsPMP25 or pOsPMP26 and 0.5 μg of pOsPMP5 having selectable markers were mixed with 50 μl of gold particle, 250 μl of 1M $CaCl_2$ and 50 μl of 0.1M spermidine rotating for 30 minutes. After washed three times with 100% ethanol, the gold particles were coated with the DNA. Following Genegun protocol provided by DuPont Inc. USA, the two plasmids were co-transformed into the calli of Taipei 309. After 45 days selection on the selective medium containing Hygromycin B, positive callus resistance to hygromycin B were further transferred on a regeneration medium under light condition for about 20 days. When the callus differentiated into plantlet, they were transferred to a rooting medium for another 15-20 days. The obtained transgenic plants were tested by PCR using target gene-specific primers. After being confirmed by PCR, the plantlets were grown in a greenhouse to produce seed, which is named as T0 generation.

Screening of High Expression Transgenic Lines

After about four months of growth, the transgenic rice plant came into flowering and producing T1 seeds. A month later, T0 generation of the transgenic rice plant came into maturation, among which 50%-60% seed-setting. After harvesting T1 seeds, high expression transgenic line was screened by Western blot from the crude extracts of rice endosperms. The expression level was analyzed with Protein Quantify ELISA (US R&D system Inc.). High expression transgenic lines were continually selected for 1-2 generations to obtain genetically stable transgenic lines. The line would then be used for large-scale production of the fusion protein.

According to the present invention, endosperms of cereal crops such as rice and barley were used to produce a soluble bioactive fusion protein. The expression level of the fusion protein using this expression system is obtained at least 0.3% brown rice dry weight, i.e., more than three grams fusion protein per kg seeds. The expression level according to the present invention is about 20 times that of a chloroplast expression system, and about 500 times that of a potato tuber expression system.

By using endosperms of cereal crops such as rice and barley as bioreactors to produce small peptides, the present invention overcomes the defects of low level expression, high cost, poor solubility; poor safety, etc. existed in conventional animal, microorganism, and other plant expression systems.

By using cereal non-storage protein as fusion carrier, the present invention effectively overcome the insolubility and difficulty for downstream processing problems of expressed fusion protein described in US patent titled "High-Level Expression of Fusion Polypeptides in Plant Seeds Utilizing Seed-Storage Proteins as Fusion Carriers" (US60/527-753).

The fusion protein system of non-storage protein of the present invention has achieved both high expression level (20-500 times more than those in conventional methods) and high solubility of the protein. It effectively solves the solubility problem caused by high level expression. The fusion protein expressed possesses bioactivities even without removing the fusion carrier, which can lower the cost up to 40-50%. The characteristics of the present invention include:

a. using non-storage proteins of cereal seed as fusion carrier to express various medicinal and health-care peptides in cereal seeds, with a expression level of more than 0.3% dry weight of seed;

b. using the promoters and signal peptides of the storage protein gene from monocotyledon crops to specifically express various medicinal and health-care peptides in seed; As an example, IGF-1 small peptide expressed in rice endosperm reaches 0.75% by dry weight of seed;

c. Said various medicinal peptides expressed in seeds refer to peptides with 20-100 amino acids, which include peptides with a variety of therapeutically and health-care uses, various types of anti-tumor peptides, various types of anti-bacteria peptides, as well as other peptides that have treatment and health-care functions to human bodies;

d. To express recombinant human insulin-like growth factor-1 in rice/barley seeds.

Abbreviations of the Expression Vectors:

pOsPMP2—a rice endosperm-specific gene expression vector.

pOsBipC—a plasmid carrying the gene of recombinant Bip-IGF-1 fusion protein.

pOsPDIC—a plasmid carrying the gene of recombinant PDI-IGF-1 fusion protein.

pOsPMP3—a plasmid carrying rice preference codes of IGF-1 gene.

pOsPMP25—a rice endosperm-specific expression vectors carrying the gene of recombinant fusion protein (Bip-C-IGF).

pOsPMP26—a rice endosperm-specific expression vectors carrying the gene of recombinant fusion protein (PDI-C-IGF).

pOsPMP5—a rice callus-specific expression vectors carrying a selectable marker.

EXAMPLE 1

Cloning of Gtl3a Promoter and Signal Peptide

To clone the promoter and signal peptide sequence of Gtl3a gene (encoding glutelin), the primers of SEQ ID NO: 1 were used to amplify the genomic DNA of Taipei 309 using a standard PCR protocol. A DNA fragment with 1284 bp was obtained. The fragment was digested by NaeI and XhoI, and then cloned to pBI221 to obtain pOsPMP2, a vector specifically expressed in rice endosperm cells (see FIG. 1). The result of DNA analysis indicated the DNA fragment apparently has promoter and signal peptide sequence (SEQ ID NO: 1).

EXAMPLE 2

Chemical Synthesis of Fusion Carrier and Target Gene with Rice Preference Genetic Codons The nucleotide sequences of rice Bip gene C-terminal (Genebank accession number: AAB63469), wheat PDI gene C-terminal (Genbank accession number: AJ277377) and insulin-like growth factor gene (Genbank accession number: CAA01955) were obtained from NCBI Databank. Analytic software MacVecter was used to covert the genes into rice preference genetic codes. The changes of optimized DNA sequence and genetic codons are shown in Table 1. It can be seen from Table 1 that all sequences of amino acids remain unchanged. The optimized genes were synthesized by US Blue Heron Biotechnology incorporation. During the synthesis process, MyII and XhoI restriction sites were added to the two ends of each gene. The genes were then cloned into pUC119 (Blue Heron Biotechnology) to produce pOsBipC, pOsPDIC and pOsPMP3, which contains BipC, PDIC and IGF-1 genes with rice preference genetic codons, respectively (SEQ ID NO: 3; SEQ ID NO: 4; SEQ ID NO: 5).

EXAMPLE 3

Constructing of Endopserm-Specific Expression Vector of Fusion Protein

Figure 2:
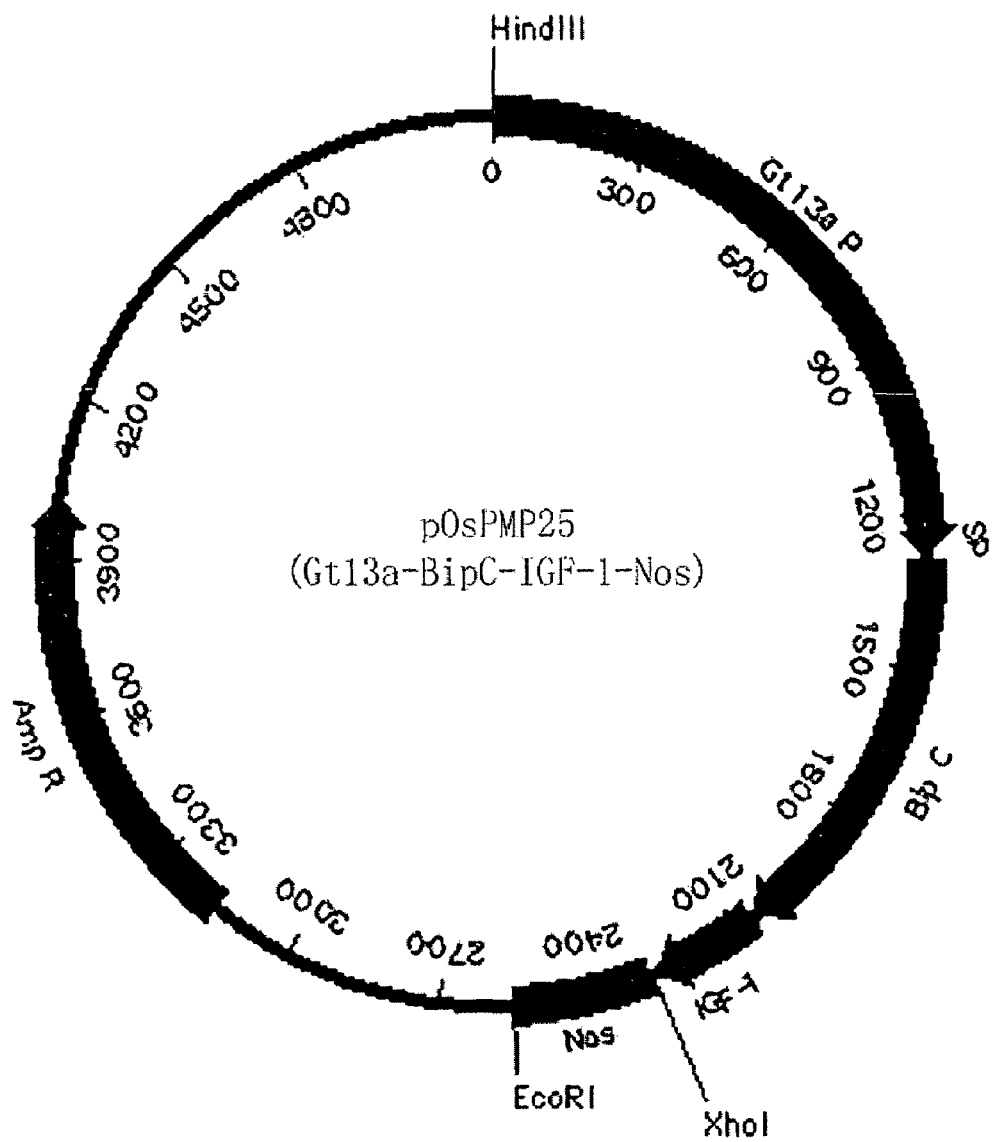
FIG. 2 is the restriction map of vector pOsPMP25 (Gtl3a-BipC-IGF-1).
Figure 3:
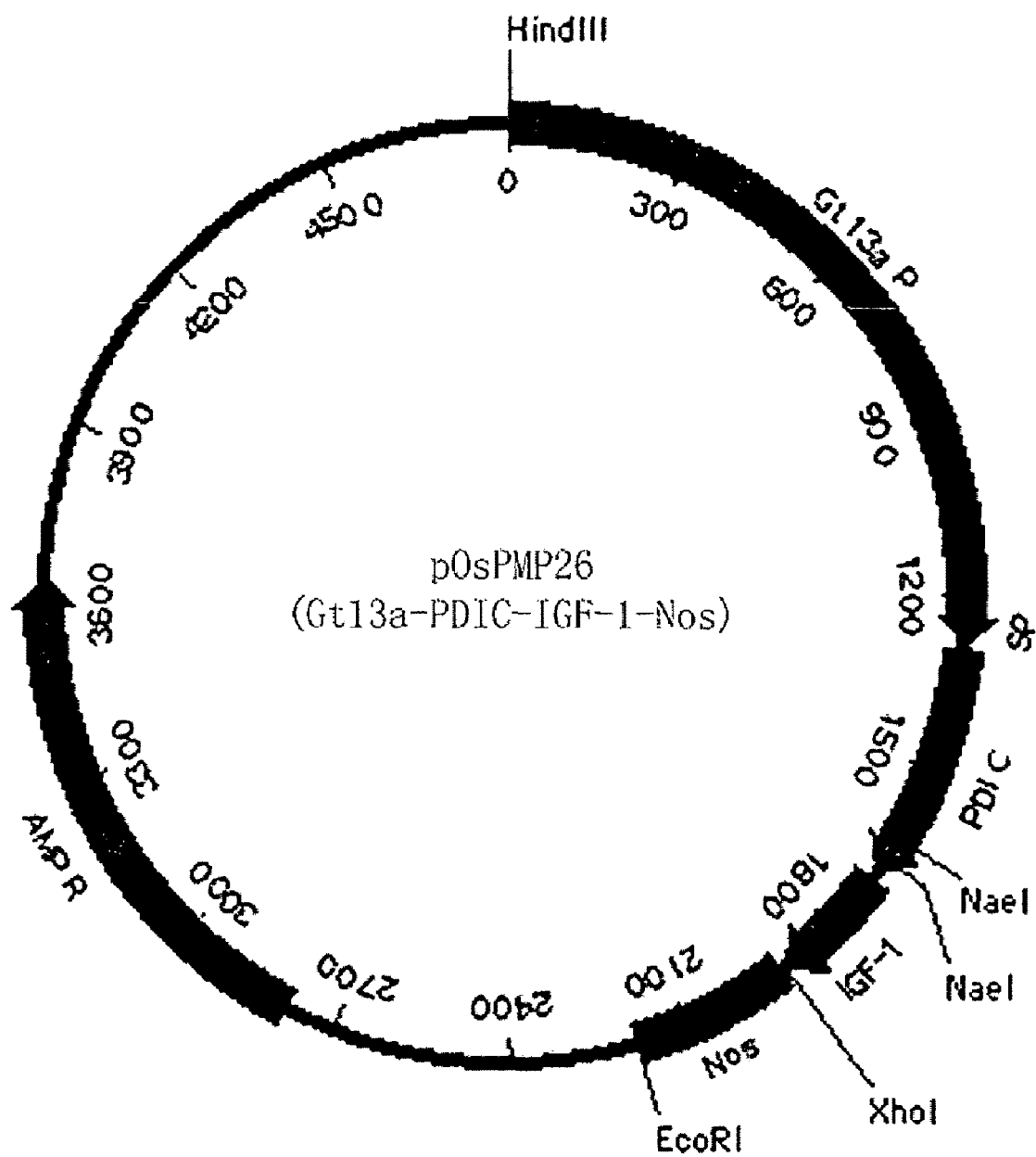
FIG. 3 is the restriction map of vector pOsPMP26 (Gtl3a-PDIC-IGF-1).

Optimized human IGF-1 was firstly amplified with PCR, and then cloned into pOsPMP2 digested with MscI and XhoI. The resultant was used to transform *E. coli* strain DH10B to produce intermediate plasmid pOsPMP3. The plasmid was digested by NaeI and NcoI, while plasmids of pOsPMP2 (See SEQ ID NO: 2), pOsBipC, and pOsPDIC were digested with appropriate restriction enzymes. The gene of the fusion carrier was ligated with pOsPMP2, and the resultant was used to transform *E. coli* strain DH10B to produce expression plasmids of pOsPMP25 and pOsPMP26. The restriction maps of the plasmids are shown in FIGS. 2 and 3.

EXAMPLE 4

Cloning of the Promoter of Rice Cysteine Proteinase β

PCR was used to produce the promoter of rice Cysteine proteinase β from rice genome. Two primers (SEQ ID NO: 6 and SEQ ID NO: 7) were designed according to the nucleotide sequence in Genbank. Following a standard PCR protocol, a positive clone 42M2 (BAC clone number) was screen from a rice artificial bacteria chromosome (BAC) library of IR64. A 5 kb fragment was obtained after the BAC clone was digested by XhoI The result of Southern blot confirmed that the fragment contains the entire nucleotide sequence of Cysteine proteinase β gene. The BAC clone was used as a template in PCR reaction to produce a DNA fragment with 1113 bp, which was further cloned into pBI221 to produce intermediate vector pOsPMP04.

EXAMPLE 5

Figure 4:
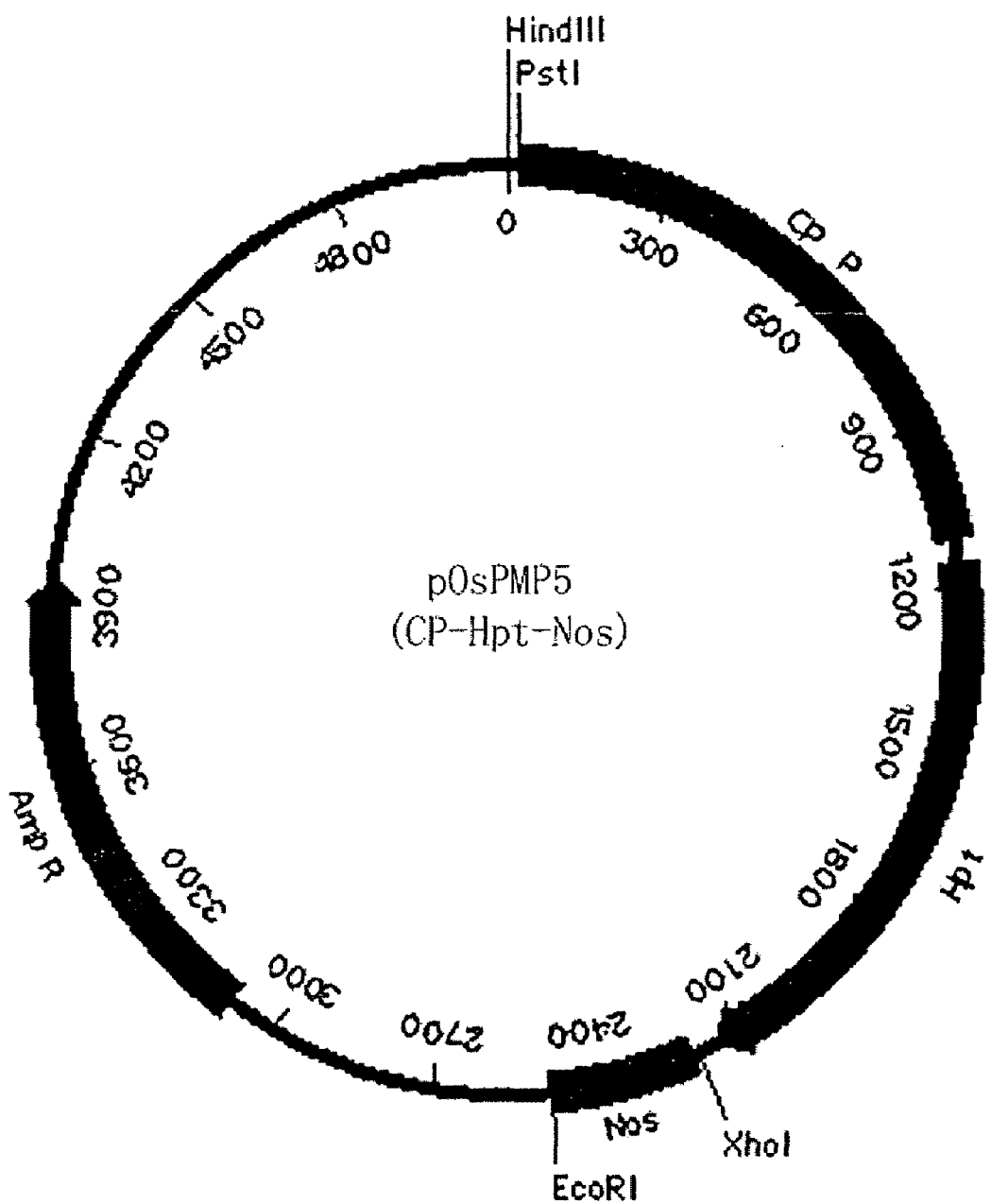
FIG. 4 is the restriction map of selective marker vector pOsPMP05 (CP-Hpt-Nos).

Constructing of Vectors with Selectable Marker Gene pCAMBIA1301 plasmid DNA was used as template in a standard PCR with a forward primer (SEQ ID NO: 8) and a reverse primer (SEQ ID NO: 9). The resultant PCR fragment was first digested with SmaI and XhoI, and then cloned into pOsPMP4 digested with NaeI and XhoI to obtain pOsPMP5, a rice callus-specific expression vector having a selectable marker (FIG. 4).

EXAMPLE 6

Transformation Mediated by Gene Gun

The seed husks of rice variety Taipei 309 were removed and the seed dehusked was sterilized in 20% sodium hypochlorite for 20 minutes, followed by washing three times with sterilized water, 10 minutes for each time. The seed was then cultured on a callus induction medium for 20-30 days to produce calli. 0.5 µg of pOsPMP25 or pOsPMP26 and 0.5 µg of pOsPMP5 having a selectable marker were mixed with 50 µl of gold particle, 250 µl of 1 M $CaCl_2$ and 50 µl of 0.1 M spermidine for 30 minutes under room temperature (20-25° C.). After washed three times with ethanol, the gold particles were coated with the DNA. Following Gene gun protocol provided by US DuPont Inc., the two plasmids were co-transformed into the callus of Taipei 309. After 45 days of screening on a selective medium containing 50 µg/ml of Hygromycin B, positive calli with hygromycin B resistance (continuously grow on the medium) were further induced on a regeneration medium under light condition for about 20 days. When the calli differentiated into small green plantlets, they were transferred to a rooting medium to culture for another 15-20 days. The obtained transgenic plants were transferred to a greenhouse to further grow until the obtaining of mature seeds.

EXAMPLE 7

Screening of Transgenic Line with High Level Expression of Fusion Protein

The transgenic plants were cultured in green houses until they went through flowering, and came into seeding. The seeds were named as Ti seeds. After harvesting, 10 seeds of each transgenic plant were homogenated in 10 ml of extracting solution (50 mM Tris, pH8.0, 50 mM NaCl, 10 mM EDTA). The solution was centrifuged for 10 minutes in a centrifuge at 14,000 g. The supernatant was tested with a Quantify ELISA kit. The result of the test indicates that the expression level of fusion protein Bip-IGF-1 is about 150 µg per seed, equivalent to 0.75% dry weight of brown seed. Transgenic individuals with high-level expression were screened repeatedly among the next generations until transgenic lines that stably express fusion proteins are obtained. The lines were then used for large-scale production of the fusion protein.

Figure 5:
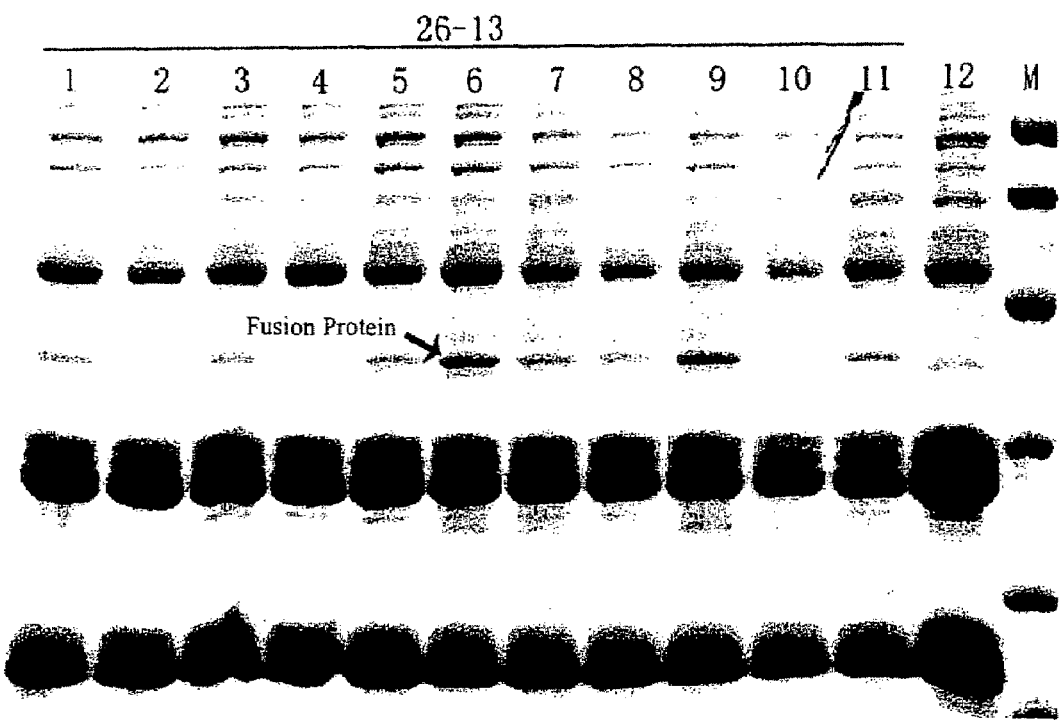
FIG. 5 is an example showing the Coomassie Blue staining of polyacrylamide gel of rice seed extracts, in which the arrow indicates that the fusion protein BipC-IGF-1 can clearly be seen while there was no corresponding band in genetically isolated single strain or Taipei 309 sample (control).
Figure 6:
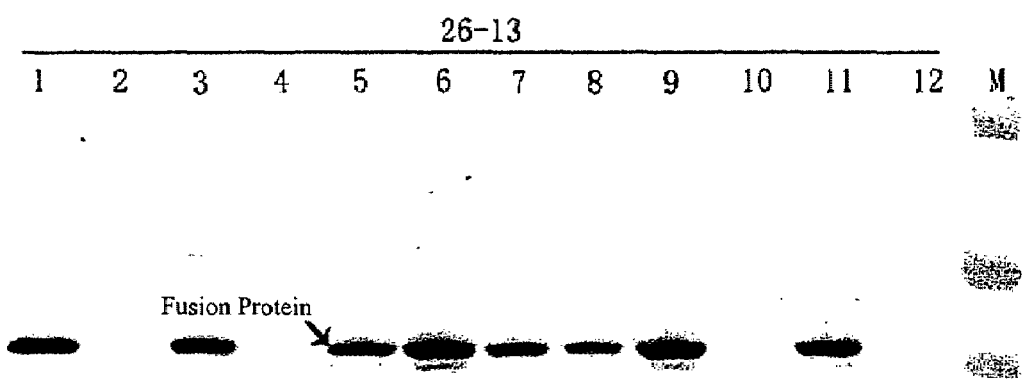
FIG. 6 shows the Western blotting using IGF-1 specific antibody, wherein the arrow indicates that the fusion protein BipC-IGF-1 can clearly be seen in the transgenic endosperm. In contrast, there was no corresponding band in genetically isolated single strain or Taipei 309 sample (control).
Figure 7:
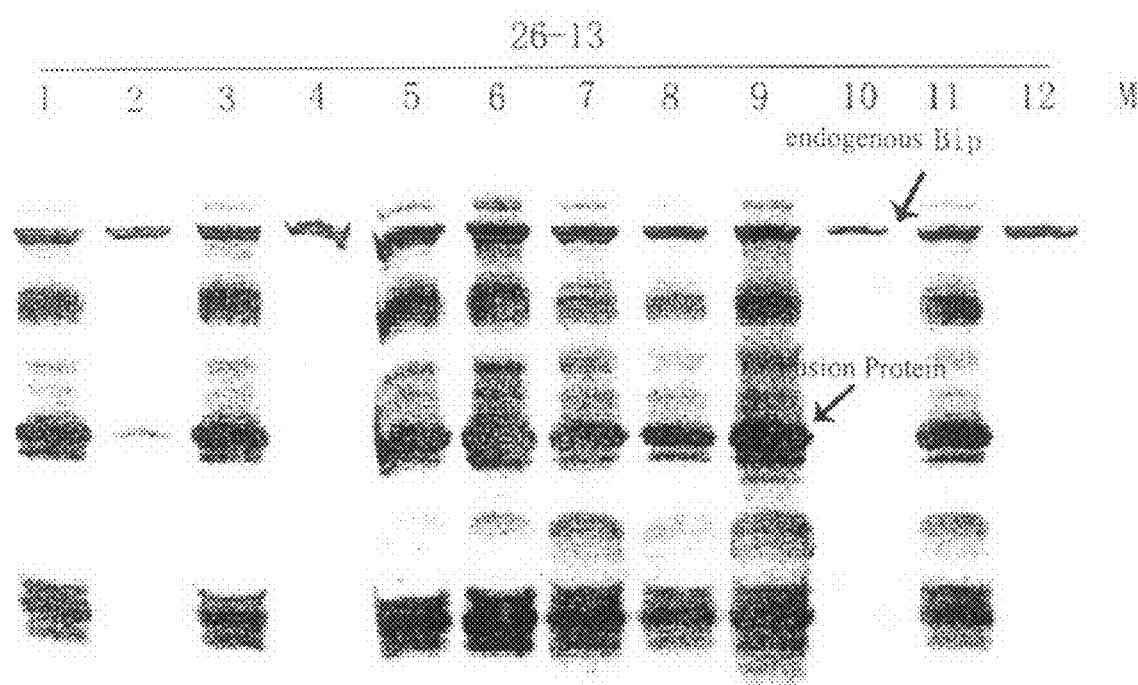
FIG. 7 shows the Western blot result when Bip specific antibody was used, wherein the arrow indicates the fusion protein BipC-IGF-1 and endogenous non-fusion Bip protein. Endogenous Bip protein and fusion protein BipC-IGF-1 exist in transgenic endosperm. In contrast, there was only endogenous Bip protein, but not recombinant fusion protein Bip-IGF-1, existed in genetically isolated single strain or Taipei 309 sample (control).

Transgenic lines with highest expression level of the fusion protein were screened from T1 seeds. To test the expression level, the crude extracts of different T1 generation lines were loaded on SDS-PAGE for electrophoresis, which was further subjected to Coomassie blue staining or Western blot. FIGS. 5-7 show the results of 11 samples from transgenic lines #26-13 and show genetically segregation. Lanes 1-11 are samples from transgenic line 26-13, wherein lanes 2, 4 and 10 are samples from genetically segregated negative individuals; lane 12 is a sample from non-transgenic variety Taipei 309 (negative control). The expression of the fusion protein can be seen clearly in polyacrylamide gel (as shown by the arrow in FIG. 5). When IGF-1 antibody was used in the test, a fusion protein with the same molecule weight as predicted can be seen in transgenic endosperm extracts. In contrast, there was no corresponding protein band existed in the extracts of non-transgenic Taipei 309 and genetically isolated negative individuals, which is consistent with the classic Mendel's law (See FIG. 6). When antibody of rice Bip was used in the test, there was only endogenous Bip protein existed in segregated negative seeds or Taipei 309 sample. In contrast, there existed two protein bands, i.e., endogenous Bip and recombinant fusion protein Bip-IGF-1, in positive transgenic seeds.

Figure 8:
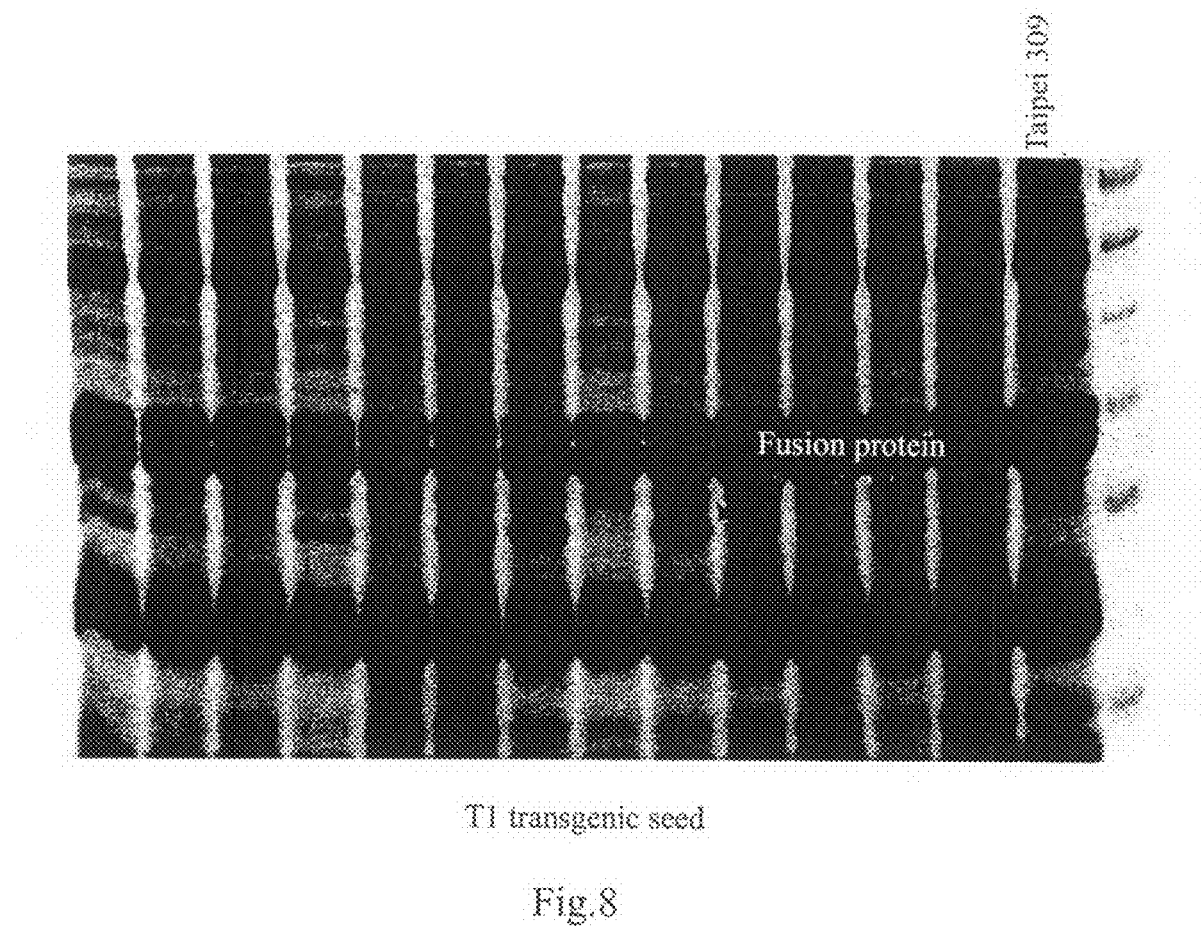
FIG. 8 is an example showing the Coomassie Blue staining of polyacrylamide gel, in which the arrow indicates that the fusion protein PDIC-IGF-1 can be seen clearly. In contrast, there was no corresponding band in genetically isolated single strain or Taipei 309 sample (control).
Figure 9:
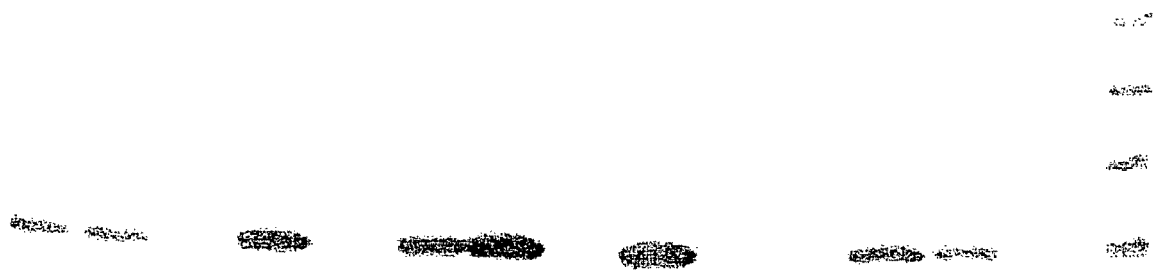
FIG. 9 shows the Western blot result when IGF-1 specific antibody was used, wherein the arrow indicates that the fusion protein PDIC-IGF-1 can be seen clearly in transgenic endosperm. In contrast, there was no corresponding band in genetically isolated single strain or Taipei 309 sample (control).

FIGS. 8 and 9 show the results of 13 samples from a transgenic line #25-12 and show genetically segregation. Lanes 1-13 are samples from transgenic line #25-12, wherein lanes 3, 5, 8, 10 and 11 are samples from genetically segregated negative seeds; lane 14 is a sample from non-transgenic variety Taipei 309 (negative control). The expression of fusion protein can be seen clearly in polyacrylamide gel (as shown by the arrow in FIG. 8). When IGF-1 antibody was used in the test, a fusion protein with the same molecule weight as predicted can be seen in the extracts from the transgenic endosperm. In contrast, there was no corresponding protein band existed in non-transgenic Taipei 309 and genetically segregated negative individuals, which is consistent with the classic Mendel's law (See FIG. 9).

What is claimed is:

1. A method of expressing a small peptide in host endosperm cells, comprising the steps of:
   (i) providing an endosperm-specific promoter and a DNA leading sequence encoding an endosperm-specific signal peptide;
   (ii) providing a polynucleotide encoding a peptide consisting of a C terminus end of protein disulfide bond dismutase (PDI) as fusion carrier, wherein said C-terminus end possesses molecular chaperone activity;
   (iii) providing a target nucleic acid encoding the small peptide, wherein the small peptide is between 20 and 100 amino acids in length;
   (iv) constructing an expression vector comprising the promoter, the DNA leading sequence, the polynucleotide encoding the fusion carrier and the target nucleic acid encoding the small peptide wherein the target nucleic acid encoding the small peptide is fused to the 3' end of the polynucleotide encoding the fusion carrier, wherein a fusion protein expressed from said expression vector comprises the small peptide fused to the C-terminus of said fusion carrier;
   (v) transforming a plant cell with the expression vector; and
   (vi) regenerating a mature plant from the transformed cell, such that seeds comprising endosperm cells are produced in which the peptide is expressed.

2. The method of claim 1, further comprising the step of optimizing at least one of DNA leading sequence, the polynucleotide encoding the fusion carrier, and the target nucleic acid encoding the small peptide such that the coding sequence comprises codons preferred by the host, before the step of constructing the expression vector.

3. The method of claim 1, further comprising the step of introducing a selectable marker into the expression vector.

4. The method of claim 1, wherein the endosperm-specific promoter and DNA leading sequence are from Gt13a gene; the host is rice, wheat or barley; the C terminus of PDI is from rice, wheat or barley; and the target nucleic acid encoding the small peptide is DNA encoding a therapeutic peptide.

5. The method of claim 4, wherein the host is rice and the therapeutic peptide is human IGF-1.

6. The method of claim 4, wherein the host is barley and the therapeutic peptide is human IGF-1.

7. The method of claim 1, wherein the C terminus of PDI from rice, wheat, or barley comprises an amino acid sequence encoded by the nucleotide sequence of SEQ ID NO: 4.

8. A method of expressing IGF-1 peptide in host endosperm cells, comprising the steps of:
   (i) providing an endosperm-specific promoter and a DNA leading sequence encoding an endosperm-specific signal peptide;
   (ii) providing a polynucleotide encoding the C terminus end of protein disulfide bond dismutase (PDI) as fusion carrier, wherein said C-terminus end of PDI possesses molecular chaperone activity;
   (iii) providing a nucleic acid encoding IGF-1;
   (iv) constructing an expression vector comprising the promoter, the DNA leading sequence, the polynucleotide encoding the C-terminus end of PDI and the nucleic acid encoding IGF-1, wherein the nucleic acid encoding IGF-1 is fused to the 3' end of the polynucleotide encoding PDI, wherein a fusion protein expressed from said expression vector comprises IGF-1 peptide fused to the C-terminus of PDI;
   (v) transforming a plant cell with the expression vector; and
   (vi) regenerating a mature plant from the transformed cell, such that seeds comprising endosperm cells are produced in which the peptide is expressed.

9. The method of claim 8, wherein the polynucleotide encoding the C-terminus end of PDI is SEQ ID NO: 4.

* * * * *

SEQUENCE LISTING

```
<160> NUMBER OF SEQ ID NOS: 9

<210> SEQ ID NO 1
<211> LENGTH: 1223
<212> TYPE: DNA
<213> ORGANISM: Oryza sativa

<400> SEQUENCE: 1
gaagaacaac tgacggtcat aaggagaggg agcttttcga taggtgccgt gcagttcaaa        60
gagttagtta gcagtaggat gaagattttt gcacatggca atgagaagtt aattatggtg       120
taggcaaccc aaatgaaaca ccaaaatatg cacaagacag tttgttgtat tctgtagtac       180
agaataaact aaagtaatga aagaagatgg tgttagaaaa tgaaacaata ttatgagtaa       240
tgtgtgagca ttatgggacc acgaaataaa aaaagaacat ttttatgagc agtgtgttct       300
caatgagcct tgaatgttat cacccaggat aagaaaccct taagcaatga aacatgcaag       360
cgtttaatgt gcaaagttgg cattctccac gacataatgc aaaagaagat ataatctatg       420
acatagcaag tcatgcatca tttcatgcct ctgtcaacct attcatttct agtcatctag       480
gtaagtatct taagctaaag tgttagaact tcccatacat aagtcataac tgatgacaat       540
tgggtgtaac acatgacaaa ccagagagtc aagcaagata aagcaaaagg atgtgtacat       600
aaaactacag agctatatgt catgttgcga aaagaggaga gcttataaga caagccatga       660
ctcaaaaaaa attcacatgc ctactgtggc ccatatatca tgcaacaatc caaaaactca       720
caggtctcgg tgttgatcgt gtcaacatgt gaccaccta aaaactcttc actaaatatt       780
aaagtattgc tagaacagag cttcaagata taagtcatga tcaccaacaa ccatgttcaa       840
aaagaaatag aaagctatgg cacagcaaca aaaagcaaaa gcatgcatgg atataatctt       900
taacatcatc catgtcatat tgcaaaagaa agaaagagag aacaatacaa atgatgtgtc       960
aattacacat ccatcattat ccatccacct tccgtgtacc acacttcata tatcatgagt      1020
cacttcatgt ctggacatta acaaactcta tcttaacatt caaatgcatg agactttatc      1080
tcactataaa tgcacaatga tttagcattg tttctcacaa aaccattcaa gttcattagt      1140
actacaacaa catggcatcc ataaatcgcc ccatagtttt cttcacagtt tgcttgttcc      1200
tcttgtgcaa tggctctcta gcc                                              1223
```

-continued

```
<210> SEQ ID NO 2
<211> LENGTH: 6038
<212> TYPE: DNA
<213> ORGANISM: Artificial Sequence
<220> FEATURE:
<223> OTHER INFORMATION: synthetic vector

<400> SEQUENCE: 2
aagcttcaac ctgctgagaa gaacaactga cggtcataag gagagggagc ttttcgatag     60
gtgccgtgca gttcaaagag ttagttagca gtaggatgaa gattttttgca catggcaatg    120 agaagttaat tatggtgtag gcaacccaaa tgaaacacca aaatatgcac aagacagttt    180
gttgtattct gtagtacaga ataaactaaa gtaatgaaag aagatggtgt tagaaaatga    240
aacaatatta tgagtaatgt gtgagcatta tgggaccacg aaataaaaaa agaacatttt    300
tatgagcagt gtgttctcaa tgagccttga atgttatcac ccaggataag aaacccttaa    360
gcaatgaaac atgcaagcgt ttaatgtgca aagttggcat tctccacgac ataatgcaaa    420
agaagatata atctatgaca tagcaagtca tgcatcattt catgcctctg tcaacctatt    480
catttctagt catctaggta agtatcttaa gctaaagtgt tagaacttcc catacataag    540
tcataactga tgacaattgg gtgtaacaca tgacaaacca gagagtcaag caagataaag    600
caaaaggatg tgtacataaa actacagagc tatatgtcat gttgcgaaaa gaggagagct    660
tataagacaa gccatgactc aaaaaaaatt cacatgccta ctgtggccca tatatcatgc    720
aacaatccaa aaactcacag gtctcggtgt tgatcgtgtc aacatgtgac caccctaaaa    780
actcttcact aaatattaaa gtattgctag aacagagctt caagatataa gtcatgatca    840
ccaacaacca tgttcaaaaa gaaatagaaa gctatggcac agcaacaaaa agcaaaagca    900
tgcatggata taatctttaa catcatccat gtcatattgc aaaagaaaga aagagagaac    960
aatacaaatg atgtgtcaat tacacatcca tcattatcca tccaccttcc gtgtaccaca   1020
cttcatatat catgagtcac ttcatgtctg gacattaaca aactctatct taacattcaa   1080
atgcatgaga ctttatctca ctataaatgc acaatgattt agcattgttt ctcacaaaac   1140
cattcaagtt cattagtact acaacaacat ggcatccata aatcgcccca tagttttctt   1200
cacagtttgc ttgttcctct tgtgcaatgg ctctctagcc ggccccggcg gggtggtcag   1260
tcccttatgt tacgtcctgt agaaacccca acccgtgaaa tcaaaaaact cgacggcctg   1320
tgggcattca gtctggatcg cgaaaactgt ggaattgatc agcgttggtg ggaaagcgcg   1380
ttacaagaaa gccgggcaat tgctgtgcca ggcagtttta acgatcagtt cgccgatgca   1440
gatattcgta attatgcggg caacgtctgg tatcagcgcg aagtctttat accgaaaggt   1500
tgggcaggcc agcgtatcgt gctgcgtttc gatgcggtca ctcattacgg caaagtgtgg   1560
gtcaataatc aggaagtgat ggagcatcag ggcggctata cgccatttga agccgatgtc   1620
acgccgtatg ttattgccgg gaaaagtgta cgtatcaccg tttgtgtgaa caacgaactg   1680
aactggcaga ctatcccgcc gggaatggtg attaccgacg aaaacggcaa gaaaaagcag   1740
tcttacttcc atgatttctt taactatgcc ggaatccatc gcagcgtaat gctctacacc   1800
acgccgaaca cctgggtgga cgatatcacc gtggtgacgc atgtcgcgca agactgtaac   1860
cacgcgtctg ttgactggca ggtggtggcc aatggtgatg tcagcgttga actgcgtgat   1920
gcggatcaac aggtggttgc aactggacaa ggcactagcg ggactttgca agtggtgaat   1980
ccgcaccctc tggcaaccgg gtgaaggtta tctctatgaac tgtgcgtcac agccaaaagc   2040
cagacagagt gtgatatcta cccgcttcgc gtcggcatcc ggtcagtggc agtgaagggc   2100
```

```
gaacagttcc tgattaacca caaaccgttc tactttactg gctttggtcg tcatgaagat    2160
gcggacttgc gtggcaaagg attcgataac gtgctgatgg tgcacgacca cgcattaatg    2220
gactggattg gggccaactc ctaccgtacc tcgcattacc cttacgctga agagatgctc    2280
gactgggcag atgaacatgg catcgtggtg attgatgaaa ctgctgctgt cggctttaac    2340
ctctctttag gcattggttt cgaagcgggc aacaagccga agaactgta cagcgaagag    2400 gcagtcaacg gggaaactca gcaagcgcac ttacaggcga ttaaagagct gatagcgcgt    2460
gacaaaaacc acccaagcgt ggtgatgtgg agtattgcca acgaaccgga tacccgtccg    2520
caaggtgcac gggaatattt cgcgccactg gcggaagcaa cgcgtaaact cgacccgacg    2580
cgtccgatca cctgcgtcaa tgtaatgttc tgcgacgctc acaccgatac catcagcgat    2640
ctctttgatg tgctgtgcct gaaccgttat tacggatggt atgtccaaag cggcgatttg    2700
gaaacggcag agaaggtact ggaaaaagaa cttctggcct ggcaggagaa actgcatcag    2760
ccgattatca tcaccgaata cggcgtggat acgttagccg gctgcactc aatgtacacc     2820 gacatgtgga gtgaagagta tcagtgtgca tggctggata tgtatcaccg cgtctttgat    2880
cgcgtcagcg ccgtcgtcgg tgaacaggta tggaatttcg ccgattttgc gacctcgcaa    2940
ggcatattgc gcgttggcgg taacaagaaa gggatcttca ctcgcgaccg caaaccgaag    3000
tcggcggctt ttctgctgca aaaacgctgg actggcatga acttcggtga aaaaccgcag    3060
cagggaggca acaatgaat caacaactct cctggcgcac catcgtcggc tacagcctcg      3120
ggaattgctc tcgagctcga atttccccga tcgttcaaac atttggcaat aaagtttctt    3180
aagattgaat cctgttgccg gtcttgcgat gattatcata taatttctgt tgaattacgt    3240
taagcatgta ataattaaca tgtaatgcat gacgttattt atgagatggg ttttatgat     3300 tagagtcccg caattataca tttaatacgc gatagaaaac aaaatatagc gcgcaaacta    3360
ggataaatta tcgcgcgcgg tgtcatctat gttactagat cgggaattca ctggccgtcg    3420
ttttacaacg tcgtgactgg gaaaaccctg gcgttaccca acttaatcgc cttgcagcac    3480
atcccccttt cgccagctgg cgtaatagcg aagaggcccg caccgatcgc ccttcccaac    3540
agttgcgcag cctgaatggc gaatggcgcc tgatgcggta ttttctcctt acgcatctgt    3600
gcggtatttc acaccgcata tggtgcactc tcagtacaat ctgctctgat gccgcatagt    3660
taagccagcc ccgacacccg ccaacacccg ctgacgcgcc ctgacgggct tgtctgctcc    3720
cggcatccgc ttacagacaa gctgtgaccg tctccgggag ctgcatgtgt cagaggtttt    3780
caccgtcatc accgaaacgc gcgagacgaa agggcctcgt gatacgccta tttttatagg    3840
ttaatgtcat gataataatg gtttcttaga cgtcaggtgg cacttttcgg ggaaatgtgc    3900
gcggaacccc tatttgttta ttttctaaa tacattcaaa tatgtatccg ctcatgagac     3960
aataaccctg ataaatgctt caataatatt gaaaaaggaa gagtatgagt attcaacatt    4020
tccgtgtcgc ccttattccc ttttttgcgg cattttgcct tcctgttttt gctcacccag    4080
aaacgctggt gaaagtaaaa gatgctgaag atcagttggg tgcacgagtg ggttacatcg    4140
aactggatct caacagcggt aagatccttg agagttttcg ccccgaagaa cgttttccaa    4200
tgatgagcac ttttaaagtt ctgctatgtg gcgcggtatt atcccgtatt gacgccgggc    4260
aagagcaact cggtcgccgc atacactatt ctcagaatga cttggttgag tactcaccag    4320
tcacagaaaa gcatcttacg gatggcatga cagtaagaga attatgcagt gctgccataa    4380
ccatgagtga taacactgcg gccaacttac ttctgacaac gatcggagga ccgaaggagc    4440
```

```
taaccgcttt tttgcacaac atggggatc atgtaactcg ccttgatcgt tgggaaccgg    4500
agctgaatga agccatacca aacgacgagc gtgacaccac gatgcctgta gcaatggcaa    4560
caacgttgcg caaactatta actggcgaac tacttactct agcttcccgg caacaattaa    4620
tagactggat ggaggcggat aaagttgcag gaccacttct gcgctcggcc cttccggctg    4680
gctggtttat tgctgataaa tctggagccg tgagcgtgg gtctcgcggt atcattgcag    4740
cactggggcc agatggtaag ccctcccgta tcgtagttat ctacacgacg gggagtcagg    4800
caactatgga tgaacgaaat agacagatcg ctgagatagg tgcctcactg attaagcatt    4860
ggtaactgtc agaccaagtt tactcatata tactttagat tgatttaaaa cttcattttt    4920
aatttaaaag gatctaggtg aagatccttt ttgataatct catgaccaaa atcccttaac    4980
gtgagttttc gttccactga gcgtcagacc ccgtagaaaa gatcaaagga tcttcttgag    5040 atccttttt tctgcgcgta atctgctgct tgcaaacaaa aaaaccaccg ctaccagcgg    5100
tggtttgttt gccggatcaa gagctaccaa ctctttttcc gaaggtaact ggcttcagca    5160
gagcgcagat accaaatact gtccttctag tgtagccgta gttaggccac cacttcaaga    5220
actctgtagc accgcctaca tacctcgctc tgctaatcct gttaccagtg gctgctgcca    5280
gtggcgataa gtcgtgtctt accgggttgg actcaagacg atagttaccg gataaggcgc    5340
agcggtcggg ctgaacgggg ggttcgtgca cacagcccag cttggagcga acgacctaca    5400
ccgaactgag atacctacag cgtgagctat gagaaagcgc cacgcttccc gaagggagaa    5460
aggcggacag gtatccggta gcggcaggg tcggaacagg agagcgcacg agggagcttc    5520 caggggaaa cgcctggtat ctttatagtc ctgtcgggtt tcgccacctc tgacttgagc    5580
gtcgattttt gtgatgctcg tcaggggggc ggagcctatg gaaaaacgcc agcaacgcgg    5640 ccttttacg gttcctggcc ttttgctggc cttttgctca catgttcttt cctgcgttat    5700
cccctgattc tgtggataac cgtattaccg cctttgagtg agctgatacc gctcgccgca    5760
gccgaacgac cgagcgcagc gagtcagtga gcgaggaagc ggaagagcgc ccaatacgca    5820
aaccgcctct ccccgcgcgt tggccgattc attaatgcag ctggcacgac aggtttcccg    5880
actggaaagc gggcagtgag cgcaacgcaa ttaatgtgag ttagctcact cattaggcac    5940
cccaggcttt acactttatg cttccggctc gtatgttgtg tggaattgtg agcggataac    6000
aatttcacac aggaaacagc tatgaccatg attacgcc                           6038
```

<210> SEQ ID NO 3
<211> LENGTH: 768
<212> TYPE: DNA
<213> ORGANISM: Artificial Sequence
<220> FEATURE:
<223> OTHER INFORMATION: synthetic C-terminal of rice preference codons
      of Bip

<400> SEQUENCE: 3

```
atcctctccg gcgagggcgg cgacgagacc aaggacatcc tcctcctcga cgtggccccg     60
ctcaccctcg gcatcgagac cgtgggcggc gtgatgacca agctcatccc gcgcaacacc    120
gtgatcccga ccaagaagtc ccaggtgttc accacctacc aggaccagca gaccaccgtg    180
tccatccagg tgttcgaggg cgagcgctcc atgaccaagg actgccgcct cctcggcaag    240
ttcgacctct ccggcatccc ggccgccccg cgcggcaccc gcagatcga ggtgaccttc    300 gaggtggacg ccaacggcat cctcaacgtg aaggccgagg acaagggcac cggcaagtcc    360
gagaagatca ccatcaccaa cgagaagggc cgcctctccc aggaggagat cgaccgcatg    420
```

```
gtgcgcgagg ccgaggagtt cgccgaggag gacaagaagg tgaaggagcg catcgacgcc    480
cgcaaccagc tggagaccta cgtgtacaac atgaagaaca ccgtgggcga caaggacaag    540
ctcgccgaca agctggagtc cgaggagaag gagaaggtgg aggaggccct caaggaggcc    600
ctggagtggc tcgacgagaa ccagaccgcc gagaaggagg agtacgagga aagctcaag     660 gaggtggagg ccgtgtgcaa cccgatcatc tccgccgtgt accagcgcac cggcggcgcg    720
ccgggcggcc gccgccgcgg ccgcctcgac gacgagcacg acgagctc                 768

<210> SEQ ID NO 4
<211> LENGTH: 399
<212> TYPE: DNA
<213> ORGANISM: Artificial Sequence
<220> FEATURE:
<223> OTHER INFORMATION: synthetic C-terminal of rice preference codons
      of PDI

<400> SEQUENCE: 4
ccggtgaagg tggtggtggc cgacaacatc cacgacgtgg tgttcaagtc cggcaagaac     60
gtgctcatcg agttctacgc cccgtggtgc ggccactgca agaagctcgc cccgatcctc    120
gacgaggccg ccgccaccct ccagtccgag gaggacgtgg tgatcgccaa gatcgacgcc    180
accgccaacg acgtgccggg cgagttcgac gtgcagggct acccgaccct ctacttcgtg    240
accccgtccg gcaagaaggt gtcctacgag ggcgccgca ccgccgacga gatcgtggac    300
tacatcaaga gaaacaagga gaccgccggc caggccgccg ccgccgccac cgagaaggcc    360
gccgagccgg ccgccaccga gccgctcaag gacgagctc                          399

<210> SEQ ID NO 5
<211> LENGTH: 399
<212> TYPE: DNA
<213> ORGANISM: Artificial Sequence
<220> FEATURE:
<223> OTHER INFORMATION: synthetic C-terminal of rice preference codons
      of IGF-1

<400> SEQUENCE: 5
ccggtgaagg tggtggtggc cgacaacatc cacgacgtgg tgttcaagtc cggcaagaac     60
gtgctcatcg agttctacgc cccgtggtgc ggccactgca agaagctcgc cccgatcctc    120
gacgaggccg ccgccaccct ccagtccgag gaggacgtgg tgatcgccaa gatcgacgcc    180
accgccaacg acgtgccggg cgagttcgac gtgcagggct acccgaccct ctacttcgtg    240
accccgtccg gcaagaaggt gtcctacgag ggcgccgca ccgccgacga gatcgtggac    300
tacatcaaga gaaacaagga gaccgccggc caggccgccg ccgccgccac cgagaaggcc    360
gccgagccgg ccgccaccga gccgctcaag gacgagctc                          399

<210> SEQ ID NO 6
<211> LENGTH: 34
<212> TYPE: DNA
<213> ORGANISM: Artificial Sequence
<220> FEATURE:
<223> OTHER INFORMATION: synthetic primer

<400> SEQUENCE: 6
cccaagcttc aacctgctga gaagaacaac tgac                                34

<210> SEQ ID NO 7
<211> LENGTH: 31
<212> TYPE: DNA
<213> ORGANISM: Artificial Sequence
```

-continued

```
<220> FEATURE:
<223> OTHER INFORMATION: synthetic primer

<400> SEQUENCE: 7
cggtgccggc tagagagcca ttgcacaaga g                              31

<210> SEQ ID NO 8
<211> LENGTH: 33
<212> TYPE: DNA
<213> ORGANISM: Artificial Sequence
<220> FEATURE:
<223> OTHER INFORMATION: synthetic primer

<400> SEQUENCE: 8
aaagtactat gaaaaagcct gaactcaccg cga                            33

<210> SEQ ID NO 9
<211> LENGTH: 35
<212> TYPE: DNA
<213> ORGANISM: Artificial Sequence
<220> FEATURE:
<223> OTHER INFORMATION: synthetic primer

<400> SEQUENCE: 9
ggagaaactc gagcttgtcg atcgacagat ccggt                          35
```